United States Patent [19]

Yamashita et al.

[11] Patent Number: 5,077,310

[45] Date of Patent: Dec. 31, 1991

[54] GRANULATION PRODUCT OF CALCIUM ASCORBATE

[75] Inventors: Junzou Yamashita, Toyonaka; Yasuo Ono, Osaka, both of Japan

[73] Assignee: Takeda Chemical Industries, Ltd., Osaka, Japan

[21] Appl. No.: 510,685

[22] Filed: Apr. 18, 1990

[30] Foreign Application Priority Data

Apr. 18, 1989 [JP] Japan ................................ 1-99711

[51] Int. Cl.$^5$ ............................................. A61K 31/34
[52] U.S. Cl. .................................................... 514/474
[58] Field of Search ........................................ 514/474

[56] References Cited

U.S. PATENT DOCUMENTS 2,442,461  6/1948  Karrer ................................... 167/81

FOREIGN PATENT DOCUMENTS 1498600  9/1967  France .
WO85/01877  5/1985  World Int. Prop. O. .......... 514/474

Primary Examiner—Frederick E. Waddell
Assistant Examiner—Zohreh A. Fay
Attorney, Agent, or Firm—Wenderoth, Lind & Ponack

[57] ABSTRACT

This invention relates to granulation products of calcium ascorbate containing a solid organic acid in an amount to make the pH of an aqueous solution of 10 g of the granulation product in 100 ml of water within the range of 5.5 to 7.0. This granulation product is prevented from being colored.

The stable granulation product of calcium ascorbate is useful for medicines, food, and in the livestock industry (as fodder), etc.

6 Claims, No Drawings

GRANULATION PRODUCT OF CALCIUM ASCORBATE

Calcium ascorbate has conventionally been supplied in the form of crystalline powders and is used in the fields of medicines, food, and in the livestock industry (as fodder), etc.

Solid preparations containing calcium ascorbate are manufactured sometimes by addition of an appropriate binder and water to calcium ascorbate followed by granulation.

While crystalline powders of calcium ascorbate are white, the granules thus obtained are yellow or yellow-brown.

This invention relates to the production of calcium ascorbate composites and granules, which are free from coloring during production.

BACKGROUND OF THIS INVENTION

Various granules containing ascorbic acid or salts thereof are produced by spraying a binder with the materials being fluidized in a fluidized-bed spray granulator, or by addition of a binder solution with the materials to be kneaded in a granulator or kneader, or by other techniques.

However, calcium ascorbate is subject to coloring during the usual procedures such as granulation by addition of a binder solution with the materials being kneaded in a kneader, or by spraying a binder with the material being fluidized in a fluidized-bed spray granulator. It is a problem that the resulting products are yellow while the starting crystalline powders of calcium ascorbate are white.

A method is disclosed in U.S. Pat. No. 2,442,461 to improve the stability of an aqueous solution of calcium ascorbate against its decomposition. This method is to add thioglycolic acid into the calcium ascorbate solution.

To stabilize calcium ascorbate powders, it has been proposed to coat the powders with hydrogenated castor oil etc.

A method is disclosed in FR 1,498,600 to improve the stability of Calcium ascorbate per se against coloring. This method consists of neutralizing the ascorbic acid with calcium carbonate in an aqueous solution containing an organic solvent to obtain white calcium ascorbate.

However, the satisfactory improvement against coloring in the granulation of calcium ascorbate has not yet been reported. And, the prior methods for producing calcium ascorbate are not sufficient to obtain the desirable product.

Thus it has been desired to produce granulation products, which are free from yellowing even in the form of solid preparations, in which calcium ascorbate itself is stable, and which can be combined easily with other ingredients such as other medicines.

DETAILED DESCRIPTION OF THE INVENTION

As a result of research on preventing the granulation products of calcium ascorbate from being colored, the inventors have found that very stable granulation products of calcium ascorbate which are free from coloring can be obtained by addition of a trace amount of an acid to the materials, and have completed the present invention based on this finding.

Namely, the invention relates to the granulation products of calcium ascorbate containing a solid organic acid in a sufficient amount to make the pH of an aqueous solution of 10 g of the granulation product in 100 ml of water within the range of 5.5 to 7.0.

The solid organic acid used in this invention is in the form of a solid at room temperature (about 0 to about 30° C.) and is water-soluble. The solid organic acid has at least "sparingly-soluble" solubility in water, preferably at least "soluble" solubility, which are indicated in the United States Pharmacopoea XXII (1990).

Among the solid organic acids usable in this invention, solid aliphatic carboxylic acids or solid enolic acids are desirable.

The aliphatic carboxylic acids include monobasic, dibasic, and tribasic acids. For example, the monobasic carboxylic acids include glycolic acid.

The dibasic aliphatic carboxylic acids are exemplified by tartaric acid, phthalic acid, maleic acid, malonic acid, malic acid, and succinic acid.

The tribasic aliphatic carboxylic acids are exemplified by anhydrous citric acid and citric acid.

Among these aliphatic carboxylic acids, dibasic and tribasic aliphatic carboxylic acids are particularly desirable. More preferably tartaric acid is used.

The enolic acids are exemplified by erythorbic acid and ascorbic acid.

The amount of an acid to be included in the granulation product is selected appropriately according to the acid to be used. The amount is determined so that the pH of an aqueous solution of 10 g of the granulation product in 100 ml of water is in the range of 5.5 to 7.0 at room temperature.

In general, the pH of an aqueous solution of 10 g of pure calcium ascorbate in 100 ml of water is around 7.2 at room temperature.

It is sometimes undesirable to make the pH of the granulation product extremely acidic. This is because calcium ascorbate is to be combined with other ingredients and also from the viewpoint of its stability. It may also be that the granulation product easily becomes yellow when the said pH shifts to the basic range over 7.0. Usually it is desirable that the pH is in the range from 5.5 to 7.0, preferably from 5.8 to 7.0. Its range, however, may be selected according to the acid to be used.

As described above, the amount of acid to be added is determined according to the solid organic acid to be used; for example, an aliphatic carboxylic acid or an enolic acid may be added in a concentration of 0.05% (W/W) or more, preferably in the range from 0.05 to 10%, more preferably 0.1 to 5%.

The granulation products of calcium ascorbate of this invention may be produced, for example, by the following techniques.

(a) Granulation by spraying a binder solution containing dissolved solid organic acid into calcium ascorbate which is fluidized in a fluidized-bed granulator.

(b) Granulation by spraying a binder solution into a mixture of calcium ascorbate and a solid organic acid flowing in a fluidized-bed granulator.

(c) Granulation by kneading calcium ascorbate with a binder solution containing dissolved a solid organic acid in a kneader.

(d) Granulation by kneading a mixture of calcium ascorbate and a solid organic acid with a binder solution which is sprayed in a kneader.

Among these techniques, the technique (a) is the most desirable, but any of the usual granulation techniques may be applied in addition to these techniques.

For the production of the granulation products of this invention, any binder may be used as far as it can usually be used for solid preparations. Water-soluble binders are particularly desirable.

The water-soluble binders are exemplified by starch paste, gelatinized starch, water-soluble cellulose derivatives and water-soluble polymers.

The water-soluble cellulose derivatives include hydroxypropylcellulose, hydroxymethylcellulose, hydroxypropylmethylcellulose, carboxymethylcellulose, and methylcellulose. The water-soluble polymers include polyvinylpyrrolidone and dextrin.

The amount of these binders to be used is in the range of 0.5 to 10 % (W/W) based on the whole granulation product, preferably 1 to 8%, more preferably 2 to 5%.

The granulation products of this invention can be produced in a desired particle size; and the products are usually used in the form of fine granules or granules.

The granulation products may additionally contain stabilizers, excipients, etc.

The granulation products of calcium ascorbate in this invention are free from coloring during production and the products obtained are also very stable and are free from yellowing.

EXAMPLES

The following examples will illustrate the invention more concretely.

EXAMPLE 1

Two kg of L-ascorbic acid and 6 kg of hydroxypropylmethylcellulose were dissolved in 63 kg of water to obtain a binder solution.

Calcium ascorbate, 192 kg, was fluidized in a fluidized-bed granulator Aeromatic FDS-6 ® (Fuji Sangyo Co., Ltd.), and granulation was performed by spraying the binder solution followed by drying under the following conditions, to give about 200 kg of calcium ascorbate granules.

Operation conditions
aeration temperature: 90° C.
aeration rate: 70 Nm$^3$/min.
spraying rate: 1.6 l/min.
spraying pressure: 3 kg/cm$^2$
drying: aeration for about 5 minutes after completion of spraying (until the exhaust gas temperature becomes 55° C.)

The composite thus obtained contained 96% of calcium ascorbate, 1% of ascorbic acid, and 3% of hydroxypropylmethylcellulose.

The pH of an aqueous solution of 10 g of the granulation product in 100 ml of water was 6.1.

EXAMPLE 2

Thirty g of tartaric acid and 270 g of hydroxypropylmethylcellulose were dissolved in 3420 g of water to obtain a binder solution.

Calcium ascorbate, 9700 g, was fluidized in a fluidization granulator Gratt WSG-15 ® (Okawara Seisakusho Co., Ltd.), and granulation was performed by spraying the binder solution followed by drying under the following conditions, to give about 10 kg of calcium ascorbate granules.

Operation conditions
aeration temperature: 90° C.
spraying rate: 140 ml/min.
spraying pressure: 1.0 kg/cm$^2$
drying: aeration for about 10 minutes after completion of spraying (until the exhaust gas temperature becomes 55° C.)

The composite thus obtained contained 97% of calcium ascorbate, 0.3% of tartaric acid, and 2.7% of hydroxypropylmethylcellulose.

The pH of an aqueous solution of 10 g of the granulation product in 100 ml of water was 6.1.

EXAMPLE 3

Two hundred g of ascorbic acid and 300 g of hydroxypropylmethylcellulose were dissolved in 3450 g of water to obtain a binder solution.

In a similar manner as in Example 2, 9500 g of calcium ascorbate was fluidized in the fluidized-bed granulator and granulation was performed by spraying the binder solution followed by drying, to give about 10 kg of calcium ascorbate granules.

The composite thus obtained contained 95% of calcium ascorbate, 2% of L-ascorbic acid, 3% of hydroxypropylmethylcellulose.

The pH of an aqueous solution of 10 g of the granulation product in 100 ml of water was 5.7.

EXAMPLE 4

Tartaric acid, 0.26 kg, and 7.47 kg of hydroxypropylmethylcellulose were dissolved in 86 liters of water to obtain a binder solution.

Calcium ascorbate, 250 kg, was fluidized in a fluidization granulator FDS-6 ® (Powrex Co., Ltd.), and granulation was performed by spraying the binder solution followed by drying under the following conditions, to give about 257 kg of calcium ascorbate granules.

Operation conditions
aeration temperature: 90° C.
spraying rate: 1,800 l/min.
spraying pressure: 1.0 kg/cm$^2$
drying: aeration for about 5 minutes after completion of spraying (until the exhaust gas temperature becomes 55° C.)

The composite thus obtained contained 97% of calcium ascorbate, 0.1% of tartaric acid, and 2.9% of hydroxypropylmethylcellulose.

The pH of an aqueous solution of 10 g of the granulation product in 100 ml of water was 6.7.

EXAMPLE 5

Tartaric acid, 0.5 g, and 29.5 g of hydroxypropylmethylcellulose were dissolved in 320 ml of water to obtain a binder solution.

Calcium ascorbate, 970 g, was fluidized in a fluidization granulator FD-6 ® (Powrex Co., Ltd.), and granulation was performed by spraying the binder solution followed by drying under the following conditions, to give about 1 kg of calcium ascorbate granules.

Operation conditions
aeration temperature: 90° C.
spraying rate: 35 ml/min.
spraying pressure: 1.0 kg/cm$^2$
drying: aeration for about 7 minutes after completion of spraying (until the exhaust gas temperature becomes 55° C.)

The composite thus obtained contained 97% of calcium ascorbate, 0.05% of tartaric acid, and 2.95% of hydroxypropylmethylcellulose.

The pH of an aqueous solution of 10 g of the granulation product in 100 ml of water was 6.95.

TEST EXAMPLE

Color changes of the granulation products of calcium ascorbate granules obtained in Examples 1 to 5 were evaluated by measuring the yellow index YI with a photoelectric colorimeter. Based upon prior experience, the color change of a yellow index of 18 or less is macroscopically unrecognizable. The control prepation of calcium ascorbate composition was obtained by granulation by spraying only a binder solution with calcium ascorbate which was fluidized in a fluidization granulator followed by drying to give 10 kg of calcium ascorbate.

The results of the test are summarized in the following table.

| Example No. | Yellow index (YI) of freshly obtained powders |
| --- | --- |
| 1 | 14.42 |
| 2 | 14.41 |
| 3 | 12.64 |
| 4 | 8.9 |
| 5 | 12.7 |
| control | 22.15 |

The YI values were obtained with a SM Color Computer ® (Suga Shikenki Co., Ltd.) differential colorimeter. The YI values, reflecting the degree of yellowing, indicate that the calcium ascorbate granules of this invention are only slightly colored.

The particle size distribution of the calcium ascorbate granules obtained in the Examples 1 to 4 is shown in the following table.

| sample | mesh proportion of the particles on the sieve | | | | | |
| --- | --- | --- | --- | --- | --- | --- |
| | 18.5 | 30 | 42 | 60 | 100 | 140 |
| Example 1 | 0 | 5.1% | 28.1% | 30.0% | 21.4% | 5.9% |
| Example 2 | 0 | 6.3 | 22.3 | 30.1 | 29.8 | 6.7 |
| Example 3 | 0 | 6.8 | 31.6 | 34.8 | 21.6 | 3.2 |
| Example 4 | 0 | 10.4 | 17.1 | 21.9 | 28.8 | 8.6 |

What we claim is:

1. A granulation product of calcium ascorbate containing a solid organic acid selected from the group consisting of tartaric acid, phthalic acid, maleic acid, malonic acid, malic acid, succinic acid, anhydrous citric acid, citric acid, erythrobic acid and ascorbic acid in an amount to make the pH of an aqueous solution of 10 g of the product in 100 ml of water within the range of 5.5 to 7.0.

2. A granulation product as claimed in claim 1, wherein the amount of the solid organic acid is the range of 0.05 to 10% (W/W) based on the whole granulation product.

3. A granulation product as claimed in claim 1, further containing a binder.

4. A granulation product as claimed in claim 3, wherein the binder is a water-soluble cellulose.

5. A granulation product as claimed in claim 3, wherein the amount of the binder is the range of 0.5 to 10% (W/W) based on the whole granulation product.

6. A granulation product as claimed in claim 1, wherein the product is in the form of granules.

* * * * *